United States Patent [19]

Green et al.

[11] Patent Number: 5,773,473
[45] Date of Patent: Jun. 30, 1998

[54] CREATINE SUPPLEMENT

[76] Inventors: Jerold L. Green; Tory E. Green, both of 205 E. 38th St., Scottsbluff, Nebr. 69361

[21] Appl. No.: 842,688

[22] Filed: Apr. 15, 1997

[51] Int. Cl.$^6$ .................................................. A61K 31/195
[52] U.S. Cl. ............................................................. 514/565
[58] Field of Search ............................................. 514/565

[56] References Cited

U.S. PATENT DOCUMENTS

| | | | |
|---|---|---|---|
| 3,988,483 | 10/1976 | Deyoe et al. | 426/53 |
| 4,600,586 | 7/1986 | Green | 426/2 |
| 5,091,171 | 2/1992 | Yu et al. | 424/642 |
| 5,397,786 | 3/1995 | Simone | 514/300 |
| 5,612,375 | 3/1997 | Sueoka | 514/565 |

FOREIGN PATENT DOCUMENTS

| | | |
|---|---|---|
| 755826-A | 11/1971 | Belgium . |
| 59-198999-A | 4/1983 | Japan . |

*Primary Examiner*—Raymond J. Henley, III
*Attorney, Agent, or Firm*—Zarley, McKee, Thomte, Voorhees, & Sease

[57] ABSTRACT

A creatine supplement is described which contains a combination of creatine and propylene glycol. The supplement preferably contains from about 25–50% creatine and from about 50–75% propylene glycol. The propylene glycol not only makes the supplement more bioavailable than conventional creatine supplements, but also decreases the incidence of side effects.

19 Claims, 2 Drawing Sheets

CREATINE SUPPLEMENT

BACKGROUND OF THE INVENTION

The present invention relates to method and means of solubilizing creatine for use as a dietary supplement. Creatine is a nitrogenous acid widely distributed in the muscular tissue of the body. It has the chemical name N-methyl-N-guanylglycine. Creatine is biosynthesized through the transamidination and transmethylation of the amino acids glycine, arginine, and methionine.

ATP is the immediate source of energy for muscle contraction. However, the amount of ATP in muscle is relatively small, so a back-up reserve supply of readily available energy is necessary. Creatine in vertebrate muscle serves as a reservoir of high-potential phosphoryl groups. Creatine phosphokinase catalyzes the reversible transfer of a phosphoryl group from creatine phosphate to ADP to form ATP as set forth in the following equation:

Creatine phosphate+ADP+H$^+$⇌ATP+creatine

The phosphoryl transfer potential of creatine phosphate is higher than that of ATP. Creatine phosphate maintains a high concentration of ATP during periods of muscular exertion. As creatine phosphate is used in muscle, the creatine moiety of the molecule is spontaneously and irreversibly converted to its anhydride creatinine. Creatinine has no known function in the body and is excreted in the urine as a waste product.

Creatine is available from many food sources. It can be found in the skeletal muscle of most mammals and fish, including beef, chicken, cod, herring, pork, salmon, tuna, and turkey. It is also present in cranberries and milk. Since most of the high creatine-containing foods are also high in fat and cholesterol, creatine supplements have become a popular source of obtaining the nutrient. Creatine monohydrate is a typical supplement available as a tasteless and odorless white powder which is combined with a liquid prior to consumption.

The body-building industry has widely promoted the benefits of creatine supplementation as a means of increasing muscle mass, strength, and energy and for reducing body fat. Once creatine enters the muscle fibers, it accumulates and stays there for several weeks. Thus, the strategy behind creatine supplementation is to fill the muscles with the nutrient to capacity and then to take only an amount sufficient to keep the creatine stores full. The creatine loading or "filling" dose is estimated from the total creatine storage capacity in the person's body, which is directly related to the person's muscle mass, as well as the person's weight and level of exercise. Recommended creatine loading dosages range from about 12–20 grams per day divided into three to four dosages. Dr. Ray Sahelian et al., *Creatine: Nature's Muscle Builder*, (1997). Maintenance doses are determined using the same factors listed above and range from about 4–12 grams per day. Id.

While there are no reports in the literature of instances regarding toxicity of creatine to the extent that creatine supplementation had to be discontinued, creatine use is associated with certain side effects. The most common side effects reported are diarrhea, gas, flatulence, nausea, and stomach cramps, with diarrhea. Sahelian, R. et al., *Creatine: Nature's Muscle Builder*, (1997). In one survey, 38% of the men and 25% of the women indicated they experienced side effects with creatine supplements. Id. The most common complaints associated with creatine supplementation is diarrhea and flatulence. This incidence of side effects increases as the creatine dose gets larger, i.e. greater then 10 grams, and by taking creatine on an empty stomach. Id. The incidence of side effects appears to decrease at creatine doses of 5 grams or less. Id.

In summary, creatine is associated with the beneficial effects of allowing muscles to store more energy, increasing strength and power, and for boosting protein synthesis and lean muscle mass. While an individual can get creatine from eating meat, the fat and cholesterol content of meat are major drawbacks to obtaining creatine in this manner. Creatine supplementation is therefore preferred over eating large amounts of meat. However, creatine doses of 5 grams and over are associated with a high incidence of side effects. In light of the fact that creatine loading doses are recommended at levels of up to 20 grams per day, it is difficult for an individual to get the recommended daily dose without taking up to five to six doses a day or by risking unwanted side effects with larger, more infrequent doses.

A research project was begun to find new techniques for formulating a creatine supplement which was more bioavailable. In doing so, the present inventors not only discovered a formulation of creatine which is more bioavailable to the user, but which also has the unexpected benefit of decreasing or eliminating the incidence of side effects associated with dosages of 5 grams or greater.

Accordingly, it is a primary object of the present invention to prepare effective formulations of creatine supplements which are useful for increasing muscle strength, power, and mass.

Another objective of the present invention is to provide creatine supplements for increasing muscle strength, power, and mass, wherein the compositions are more bioavailable than conventional creatine supplements.

Another objective of the present invention is to provide creatine in a supplement which does not cause adverse side effects.

The method and means of accomplishing each of the above objectives as well as others will become apparent from the detailed description of the invention which follows hereinafter.

SUMMARY OF THE INVENTION

Figure 1:
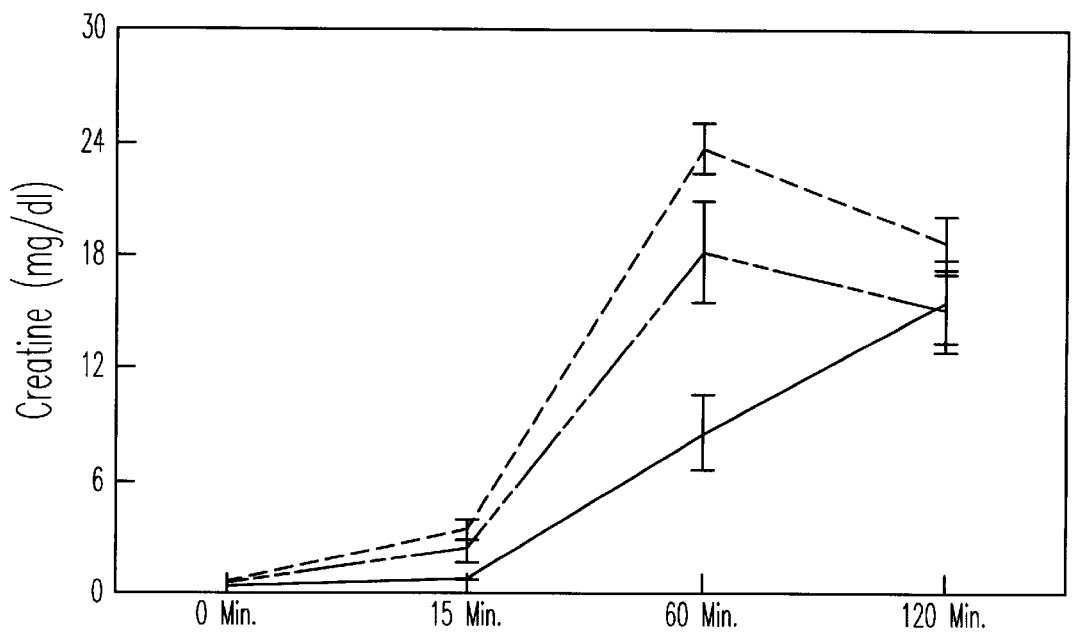
FIG. 1 is a cumulative graph of the graphs set forth in FIGS. 2–4 illustrating the creatine levels of individuals at various intervals over a 120 minute time period. The results are from three separate trials involving the creatine supplement of the present invention (New Creatine™) and trials using two conventional creatine supplements, EAS® and P-HP®, wherein each of the individuals took a one-time 7.5 gram dose of one of the above-referenced supplements.

The invention relates to a method and composition for increasing muscle strength, power, and mass with supplemental creatine, its pro drugs and analogues. The creatine formulation provides increased creatine bioavailability, and decreases or completely eliminates the side effects associated with conventional supplements. The formulations comprise creatine in combination with propylene glycol.

DETAILED DESCRIPTION OF THE INVENTION

The present invention relates to new formulations of creatine supplements which demonstrate increased bioavailability and fewer side effects than conventional creatine supplements. Creatine has the formula:

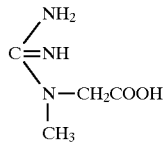

When the term "creatine" is used herein it is understood that it contemplates not only the compound itself but pro drugs which metabolize to the compound and analogues and biologically active salt forms thereof, as well as optical isomers which provide the same pharmaceutical result. While creatine monohydrate is the form of creatine which is conventionally used in supplements, the present invention also contemplates the use of other creatine salts, such as creatine kinase, creatine phosphate, and creatine phosphokinase.

As earlier mentioned, creatine supplementation has been associated with an increase in muscles' ability to store energy, an increase in muscle strength and power, a boost in protein synthesis, and an increase in lean muscle mass, as well as a subsequent decrease in body fat. Since creatine is a nutrient normally found in body tissue, its toxicity as a supplement is very low.

This invention is predicated upon the discovery that creatine mixed with propylene glycol can be formulated into a supplement which has increased bioavailability and which also has fewer side effects than conventional creatine supplements. The important point is that previously any dosages of creatine 5 grams or greater had a high incidence of side effects, particularly diarrhea, gas, and bloating. For persons taking a loading dose of 20 grams creatine daily, it was difficult to take this full dosage amount over the course of the day without the risk of getting these side effects. It had not been discovered that creatine mixed with propylene glycol would produce a formulation which was not only more bioavailable than previously available supplements, but which also results in a lower incidence of diarrhea, gas, and bloating.

The major ingredients of the creatine supplement in accordance with the present invention are creatine and propylene glycol. The preferred form of creatine is creatine monohydrate. The amount of creatine in the composition can vary from about 5% to about 95% by weight. The preferred range of creatine is from about 25–50% by weight and the most preferred range is from about 25–35% by weight.

The other major ingredient of the composition is propylene glycol. Other glycols are also appropriate for use in the instant invention, including ethylene glycol, diethylene glycol, triethylene glycol, and dipropylene glycol. The amount of propylene glycol in the composition is from about 5–95% by weight. The preferred range of propylene glycol is from about 50–75% by weight and the most preferred range is from about 65–75% by weight.

If one bases the amount of propylene glycol present in the composition on the amount of creatine, it is preferred that the amount be from 2–3 parts propylene glycol to 1 part creatine.

It is also contemplated that certain minors can be added to the composition. However, it should be understood that the term "minors" is not being used from the standpoint of their effect on the composition, but merely from the standpoint of a characterization of the amount that is present in comparison with the higher weight percent levels of creatine and propylene glycol. These minors include, but are not limited to, flavorings, dyes, lubricants, binders, fillers, vitamins, minerals, and amino acids. Because it is likely that the present composition will primarily be used by body builders and weight lifters, other appropriate minors include liquid carbohydrates, such as glucose and fructose solutions for an additional source of energy. These minor ingredients will typically comprise from about 0.1–5.0% of the composition.

In accordance with the method of this invention, there is no particular order or method that must be used to prepare the creatine composition. The only requirement is that the ingredients be combined homogenously. A preferred method involves the use of a high shear and high speed mixing device to combine the ingredients more efficiently and completely. If liquid carbohydrates are included in the composition, it is preferred that the liquid carbohydrates be combined first with the propylene glycol since these ingredients are more compatible. The creatine is added thereafter.

If minerals are added to the composition, they will chelate or coordinate with the propylene glycol. Fat soluble vitamins form a covalent adduct with propylene glycol by reversible conjugate addition and/or are involved in nucleophilic displacement or reversible hemiketal formation. Water soluble vitamins and amino acids both have improved mass action solubility because of their soluble nature in propylene glycol.

The temperature during the admixing does not appear to be important. Satisfactory results are obtained when the ingredients are combined at room temperature.

As set forth above, the composition of the present invention is normally dosed in an amount of from about 12–20 grams per day and at a maintenance dose of from about 4–12 grams per day. Higher or lower doses may also be appropriate based on the characteristics of the individual. Since the present composition does not have the incidence of side effects that is present with conventional creatine supplements, the dose can easily be increased to an amount higher than 20 grams per day without the need for taking the creatine five to six times daily.

While creatine is conventionally supplemented in a loose powder form, it is also contemplated that it can be contained in a variety of other dosage forms. In general, in addition to the active compounds i.e. creatine and propylene glycol, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, drageemaking, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitol and/or dextran. Optionally, the suspension may also contain stabilizers.

In addition to administration with conventional carriers, active ingredients may be administered by a variety of specialized delivery drug techniques which are known to those of skill in the art, such as portable infusion pumps.

While the applicant does not wish to be bound by any theory, it is believed the creatine supplement of the present invention is more bioavailable than conventional supplements because the propylene glycol acts as an effective mainline carrier of the creatine into the bloodstream. Further, it is believed that the composition is also associated with less gastrointestinal-related side effects, such as gas, bloating, and diarrhea, since the composition is absorbed more quickly into the bloodstream and spends less time in the stomach and intestine.

The following examples are offered to further illustrate but not limit the process, composition or method of the invention.

EXAMPLE

Materials and Methods

A trial involving the creatine supplement of the present invention processed with propylene glycol (New Creatine™) versus two available creatine supplements, EAS® and P-HP®, was conducted at the University of California, San Diego. Three groups of five individuals were used in each trial.

In each of the three trials, five individuals took 7.5 grams of either the EAS, P-HP, or New Creatine. Blood was drawn and tested from amounts of creatine in 15 minute intervals for all subjects. The results are set forth in FIGS. 1–4.

Results

Figure 3:
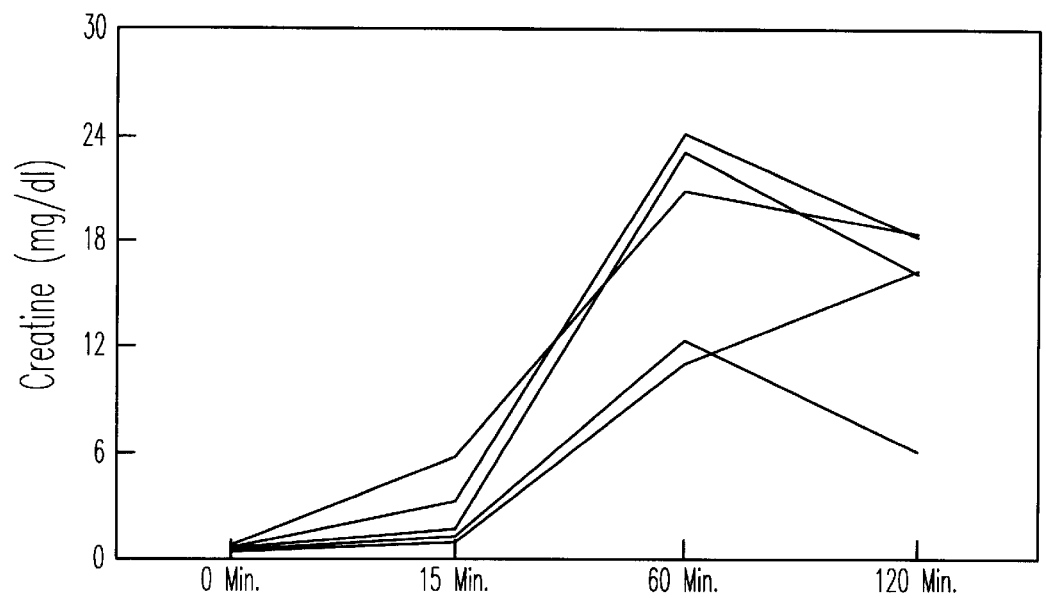
FIG. 3 is a graph illustrating the creatine levels of five individuals who each took a 7.5 gram dose of P-HP®. The results are calibrated at 15 minute intervals over a 120 minute time period.
Figure 4:
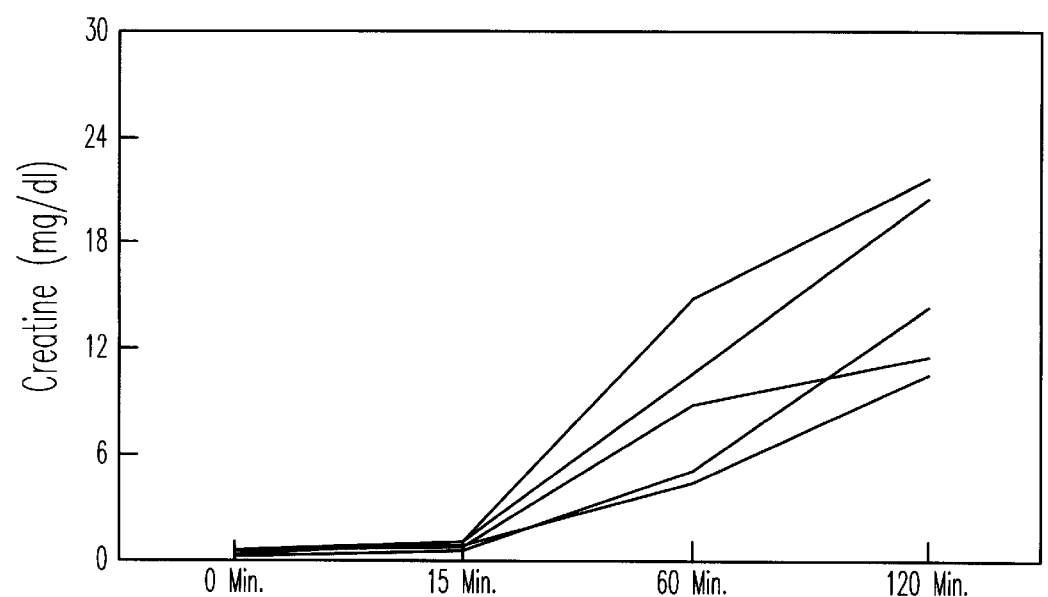
FIG. 4 is a graph illustrating the creatine levels of five individuals who each took a 7.5 gram dose of EAS®. The results are calibrated at 15 minute intervals over a 120 minute time period.

All subjects who took New Creatine showed the presence of creatine in their blood within the first 15 minutes after the 7.5 gram dose. The subjects taking the P-HP and EAS products did not consistently show blood levels of creatine in the first fifteen minutes of the test. As best shown by FIGS. 3 and 4, some of the P-HP and EAS subjects did not show any levels of creatine in their bloodstreams within the first fifteen minutes.

Figure 2:
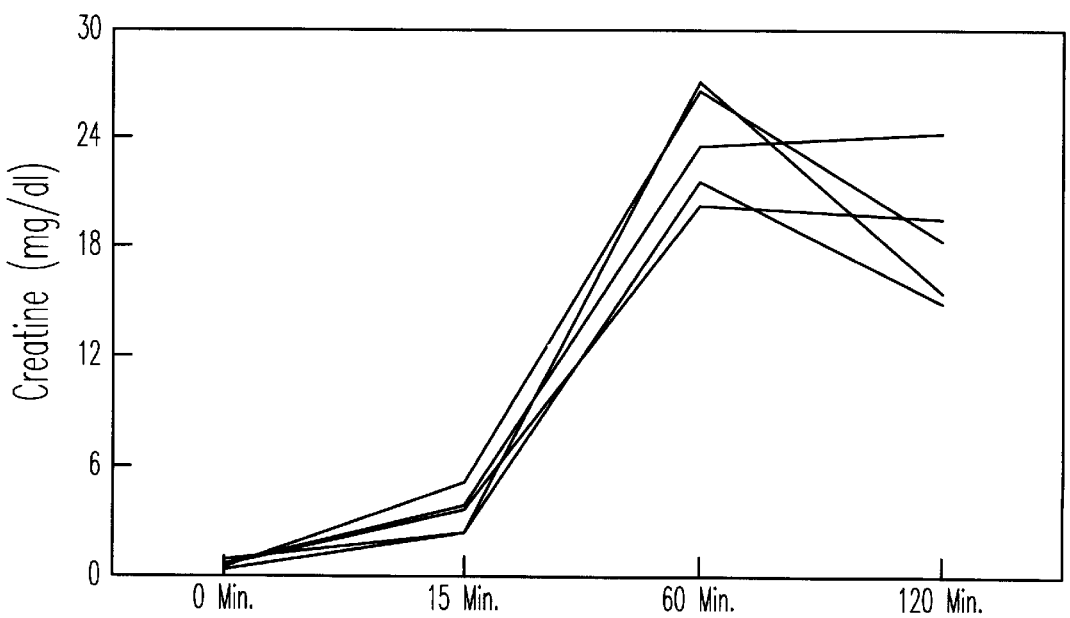
FIG. 2 is a graph illustrating the creatine levels of five individuals who each took a 7.5 gram dose of New Creatine™. The results are calibrated at 15 minute intervals over a 120 minute time period.

FIG. 1 is a cumulative graph of the creatine levels of the subjects from the three trials. FIGS. 2–4 are graphs of the results of the individual trials using New Creatine, P-HP, and EAS, respectively. The graphs demonstrate that the subjects taking New Creatine got higher levels of creatine in their bloodstreams faster than the subjects taking the P-HP or EAS. Not only did the subjects have more creatine in their blood at the end of 60 minutes, but they also maintained higher creatine levels at the end of 120 minutes.

In addition, the subjects taking New Creatine reported feeling the beneficial effects of the creatine on a consistent basis while the subjects taking the other supplements did not.

Moreover, the subjects taking New Creatine reported that the flatulence problem was virtually eliminated while the subjects taking P-HP and EAS still reported incidents of gas and diarrhea.

It can be seen from the above trials that creatine mixed with propylene glycol is more bioavailable than creatine supplements without propylene glycol. Further, the creatine/propylene glycol supplement is associated with fewer side effects than conventional creatine supplements. It is therefore submitted that the present invention accomplishes at least all of its stated objectives.

While the present invention has been shown in certain embodiments and dosages, it is contemplated that minor dosage and formulation modifications of the composition and the ranges expressed herein may be made and still come within the scope and spirit of the present invention.

What is claimed is:

1. An internal creatine supplement consisting essentially of:
   25–50% creatine monohydrate by weight; and
   50–75% of a glycol by weight;
   said creatine and glycol in a pharmaceutically acceptable vehicle for internal administration.

2. A creatine supplement according to claim 1 wherein the glycol is selected from the group consisting of propylene glycol, ethylene glycol, diethylene glycol, triethylene glycol, and dipropylene glycol.

3. A creatine supplement according to claim 2 wherein the glycol is propylene glycol.

4. A creatine supplement according to claim 1 wherein the supplement is from about 25–35% creatine and from about 65–75% glycol by weight.

5. A creatine supplement according to claim 1 wherein the supplement further includes nutrients selected from the group consisting of vitamins, minerals, amino acids, and liquid carbohydrates.

6. A creatine supplement according to claim 1 wherein the supplement further includes a suitable pharmaceutical excipient selected from the group consisting of fillers, lubricants, binders, colorings, and flavorings.

7. The creatine supplement according to claim 1 wherein the supplement is in a pharmaceutical carrier selected from the group consisting of a tablet, capsule, cream, ointment, solution, cream, gel, suspension, suppository, or spray.

8. A method of preparing a creatine supplement for internal administration consisting essentially of:
   combining 25–50% by weight of creatine monohydrate with 50–75% by weight propylene glycol; and
   placing the creatine monohydrate, propylene glycol, and excipient in a pharmaceutically acceptable vehicle for internal administration.

9. A method according to claim 8 wherein the creatine and propylene glycol are homogenously mixed.

10. A method according to claim 8 including the addition of ingredients selected from the group consisting of vitamins, minerals, amino acids, and liquid carbohydrates.

11. A method according to claim 8 wherein the creatine and propylene glycol are combined with a high shear mixer.

12. A method of preparing a creatine supplement comprising:
    combining a supplementation amount of creatine with propylene glycol and additional ingredients selected from the group consisting of vitamins, minerals, amino acids, and liquid carbohydrates;
    wherein the liquid carbohydrate and propylene glycol are combined first to form a mixture, and the creatine is combined with the mixture thereafter.

13. A method of increasing muscle mass and strength comprising:
    ingesting a supplement comprising creatine and propylene glycol.

14. A method according to claim 13 wherein the dosage of supplement ingested is from about 4–20 grams per day.

15. A method according to claim 13 wherein the dosage of 4–20 grams per day is ingested in increments 5 grams per dose or larger.

16. A method according to claim 13 wherein the supplement comprises 5–95% creatine and 5–95% propylene glycol by weight.

17. A method according to claim 16 wherein the supplement comprises 25–50% creatine and 50–75% propylene glycol by weight.

18. A method according to claim 17 wherein the supplement comprises 25–35% creatine and 65–75% propylene glycol by weight.

19. A method of increasing muscle mass and strength comprising:
    internally administrating a supplement comprising creatine and a glycol.

* * * * *